United States Patent [19]
Arteman et al.

[11] Patent Number: 5,925,026
[45] Date of Patent: *Jul. 20, 1999

[54] APERTURED ABSORBENT PADS FOR USE IN ABSORBENT ARTICLES

[75] Inventors: David Jerome Arteman, Appleton; Nancy Jo Myers, Dale, both of Wis.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/813,934

[22] Filed: Mar. 10, 1997

[51] Int. Cl.$^6$ .................................................. A61F 13/15
[52] U.S. Cl. ......................................... 604/383; 604/380
[58] Field of Search ................................ 604/379, 380, 604/382, 383, 385.1

[56] References Cited

U.S. PATENT DOCUMENTS

| | | | |
|---|---|---|---|
| 2,788,003 | 4/1957 | Morin | 604/380 |
| 3,344,789 | 10/1967 | Arnold et al. | |
| 3,403,681 | 10/1968 | Hoey et al. | 604/383 |
| 3,441,021 | 4/1969 | Endres | |
| 3,703,897 | 11/1972 | Mack et al. | |
| 3,814,101 | 6/1974 | Kozak | 604/370 |
| 3,881,490 | 5/1975 | Whitehead et al. | |
| 3,886,941 | 6/1975 | Duane et al. | |
| 3,927,673 | 12/1975 | Taylor | |
| 4,027,672 | 6/1977 | Karami | 604/385.1 |
| 4,059,114 | 11/1977 | Richards | |
| 4,424,249 | 1/1984 | Rupinskas | |
| 4,443,512 | 4/1984 | Delvaux | 604/380 |
| 4,650,481 | 3/1987 | O'Connor et al. | |
| 4,758,240 | 7/1988 | Glassman | |
| 4,762,521 | 8/1988 | Roessler et al. | |
| 4,795,455 | 1/1989 | Luceri et al. | |
| 4,886,632 | 12/1989 | Van Iten et al. | |
| 4,936,839 | 6/1990 | Molee et al. | |
| 5,009,651 | 4/1991 | Kamishioiri et al. | |
| 5,104,396 | 4/1992 | Oatley et al. | |
| 5,188,625 | 2/1993 | Van Iten et al. | |
| 5,300,053 | 4/1994 | Genaro | |
| 5,486,166 | 1/1996 | Bishop et al. | |
| 5,490,846 | 2/1996 | Ellis et al. | |
| 5,669,895 | 9/1997 | Murakami et al. | 604/380 |

*Primary Examiner*—John G. Weiss
*Assistant Examiner*—Dennis Ruhl
*Attorney, Agent, or Firm*—Michael L. Winkelman; Thomas D. Wilhelm; Brian R. Tumm

[57] ABSTRACT

This invention relates to absorbent pads, and methods for fabricating absorbent pads, having improved fluid intake and preferential wicking in the longitudinal direction. The absorbent pads have patterns of apertures which encourage the preferential wicking. The apertures are characterized by size, spacing from each other, and depth of penetration into the absorbent pad, such that fluid intake rate is increased and distribution of fluid in the longitudinal direction is improved. Apertures are preferably spaced close enough to each other that aqueous liquid is preferentially transferred from aperture to aperture by capillary effect, along the length of the absorbent pad. Preferential wicking between apertures in the longitudinal direction increases the overall effective liquid absorption rate of the absorbent pad, thereby increasing overall effective liquid capacity of the respective absorbent article. A novel method of fabricating an absorbent pad of the invention includes penetrating into but not through the absorbent pad using heated pin elements. The heated pin elements form a plurality of apertures in a first surface of the pad, the pad having higher density proximate the apertures than the overall density of the absorbent pad. The lower density areas of the pad have greater aqueous intake rates than higher density portions of the absorbent pad.

57 Claims, 6 Drawing Sheets

FIG. 11 though the pad, along the length of the absorbent pad, rather than across the width of the pad. Preferential wicking between apertures in the longitudinal direction increases the overall effective liquid absorption rate of the absorbent pad, because absorbed liquid is rapidly transported away from the locus of absorption, thus voiding space at the locus of absorption, which voided space can be used for rapidly absorbing additional quantities of liquid. The perceived value of the invention is in thus increasing the overall effective capacity of the absorbent article to absorb liquid over a relatively short time period representative of conditions of use in absorbing body exudates.

APERTURED ABSORBENT PADS FOR USE IN ABSORBENT ARTICLES

FIELD OF THE INVENTION

The present invention relates to apertured pads for use in absorbent articles. More particularly, the invention relates to patterns of apertures, sizes of the apertures, depths of the apertures, and other aspects of apertured absorbent pads that improve both the intake rate for receiving aqueous fluid thereinto, movement of the liquid within the absorbent pad, and the overall effective ability of the pad to receive the liquid and move the liquid along the length of the absorbent pad.

BACKGROUND OF THE INVENTION

Absorbent pads are well known for use in absorbent articles. Absorbent pads may be located e.g. between the bodyside liner and the outer cover of an absorbent article. Absorbent pads receive and retain liquid from the body of a user. The absorbent pad must be effective to receive, from the body of the user, and to retain, a sufficient quantity of liquid to prevent leaking of the liquid from the absorbent article.

It is known to use apertures in absorbent articles to help channel liquids away from the body of the wearer and into the absorbent material of the absorbent article. In conventional such use, a liner sheet of the absorbent pad is bonded to an absorbent body of the absorbent pad. In some such conventional embodiments, apertures extend through the absorbent body, and the liner sheet extends through the aperture and is bonded to the backing sheet or a bonding sheet on the opposite side of the absorbent pad.

There is also known a quilted diaper having apertures extending entirely through the absorbent pad. An inner sheet is secured to a back sheet in the apertures. An intervening layer having smaller apertures may be located between the inner sheet and the absorbent pad.

It is also known to have a disposable insert for a diaper wherein the insert has an impermeable, but slitted, top sheet. The slits extend entirely through the top sheet, and may open and allow liquid to pass through, thereby to enter an underlying absorbent pad until the pad is saturated. As liquid is received into the absorbent pad, dimples in the absorbent pad expand, and close the slits, permitting substantially no entry or exit of liquid from the absorbent pad after the absorbent pad becomes saturated with the liquid.

SUMMARY OF THE DISCLOSURE

This invention relates to absorbent pads, especially absorbent pads used for absorbing body exudates, and methods for fabricating such absorbent pads, having improved fluid intake rates, and preferential wicking along the longitudinal dimension of the pad. The absorbent pads have patterns of apertures which encourage the preferential wicking. The apertures are characterized by size, spacing from each other, and depth of penetration into the absorbent pad, as well as increased density of fibrous material of the pad about and proximate the surfaces of the apertures, such that fluid intake rate is increased and distribution of fluid in the longitudinal direction is improved, over rates and distribution of conventional pads.

Apertures are preferably spaced sufficiently close to each other that aqueous liquid is transferred from aperture to aperture by capillary effect. Spacing and arrangement of the apertures in the aperture array is such as to facilitate traverse A novel method of fabricating an absorbent pad of the invention includes penetrating into but generally not through the absorbent pad, using heated pin elements. The heated pin elements form a plurality of apertures in a first surface of the pad. The pad has higher density proximate the apertures than the overall density of the absorbent pad. The lower density areas of the pad have greater aqueous intake rates than higher density portions of the absorbent pad.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. Further, the above drawings are not drawn to scale and do not so limit the invention.

DETAILED DESCRIPTION OF THE ILLUSTRATED EMBODIMENTS

The present invention is directed toward an absorbent article having increased fluid intake rate and improved distribution of fluid. The invention includes an absorbent pad having a number of apertures arranged in a pattern to promote wicking in the longitudinal direction. The number of apertures, the surface area of the apertures, and the depths of the apertures, all contribute, in combination, to the improved wicking effect, and distribution, of liquid. Another benefit of the invention is that the apertures improve the structural integrity of the absorbent pad.

Throughout the disclosure and claims, the phrase "absorbent article" means infant care, adult care and feminine care products which absorb fluids from the body of the user.

Throughout the disclosure and claims, the word "fluid" means flowable elements of urine, feces containing liquid, menses, and any other bodily fluid that can be transferred from a user to an absorbent article.

The terms "densification" and/or "densified" defines portions of an absorbent pad which have a higher density of fibrous material, such as cellulosic fluff, than the overall average density of the respective absorbent pad. Such densification does, however, leave sufficient open space in the matrix of fibers to readily receive aqueous liquids thereinto in absorbing liquids into pad 10.

Figure 1:
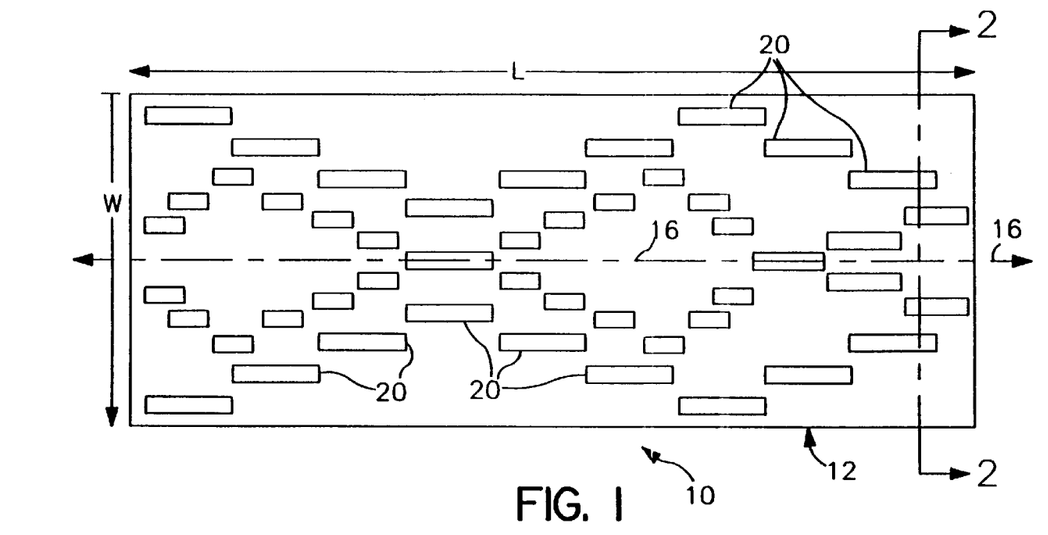
FIG. 1 shows a top view of a first embodiment of an absorbent pad of the invention.
Figure 2:
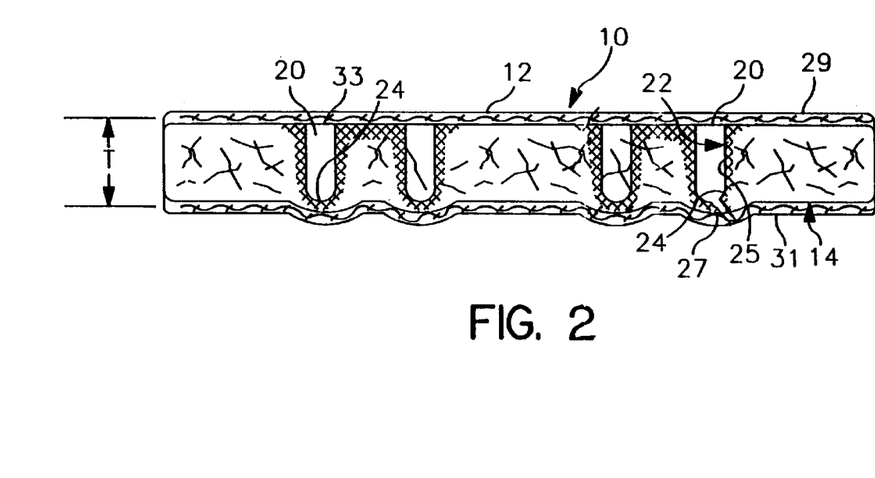
FIG. 2 shows a cross-section of the absorbent pad taken at 2—2 in FIG. 1.

FIGS. 1 and 2 illustrate a first absorbent pad 10 of the invention. Absorbent pad 10 includes a first apertured surface 10 and a second opposing reference surface 14. Absorbent pad 10 has a length "L," a width "W," shown in FIG. 1, and a thickness "T," shown in FIG. 2. Second reference surface 14 preferably has no apertures, or few apertures. Absorbent pad 10 has a longitudinal axis 16 extending along the length thereof. A multiplicity of apertures 20 extend from first surface 12 inwardly into the absorbent pad toward second reference surface 14, and generally terminate as blind apertures at respective bottoms 24. Apertures 20 are typically formed, in a nip, by heated pin elements.

The absorbent pad material around apertures 20 is more dense than portions of absorbent pad 10 which are spaced from the apertures. Such denser zones about apertures 20 encourage wicking of fluid into the denser zones. Preferred embodiments have aperture patterns which preferentially wick fluid longitudinally along the length of absorbent pad 10 and away from the center thereof. Thus apertures 20 improve the overall distribution of fluid in absorbent pad 10. Surprisingly, the number of apertures, spacing of apertures, and the arrangement of the apertures in the aperture array can also improve the intake rate of absorbent pad 10. Therefore, the intake rate and the pattern of distribution of liquid within the absorbent pad 10 is improved in the invention.

Exemplary apertures 20 shown in FIG. 1 are rectangular. Such rectangular apertures can have a length of up to about 1 inch and a width of up to about ¼ inch. As illustrated in FIG. 1, some or all of the apertures can have smaller sizes. Indeed, in some embodiments of the invention, all the apertures have substantially the same size, both cross-sectional dimensions and depths. However, aperture cross-sections and aperture depths can differ for different apertures in the same absorbent pad.

As shown in FIG. 1, the lengths of rectangular apertures 20 extend along the length "L" of absorbent pad 10.

In preferred embodiments, substantially none of apertures 20 extend through absorbent pad 10 and thus penetrate surface 14. As shown in FIG. 2, apertures 20 generally extend from first surface 12 inwardly of the absorbent pad for about 90% of the dimension of thickness "T" of absorbent pad 10. As shown in FIG. 2, each aperture 20 has an inner aperture surface 22 extending from first surface 12 toward bottom 24, and including the perimeter sidewalls 25 on the interior of the aperture. During manufacture or during later handling, some or all of bottoms 24 may rupture as shown at 27 in FIG. 2, such that the respective aperture extends in principle entirely through absorbent pad 10. Generally, however, bottoms 24 are closed as shown at the apertures illustrated on the left side of FIG. 2. However, even where the bottom is ruptured as at 27, the size of the open area of the opening so created is small by comparison to the open cross-sectional area (top view) of the main body of the respective aperture 20. In any event, ruptures 27 represent bottoms 24 in which openings have been created, and wherein bottoms 24 generally remain intact, though ruptured. Second reference surface 14 has outward bulges substantially corresponding to apertures 20 as shown in FIG. 2. Each such densified outward bulge can be considered an outer bottom surface corresponding to each respective aperture 20.

Absorbent pad 10 suitably comprises a matrix of hydrophilic fibers, such as a web of cellulosic fluff. Optionally, a high-absorbency material commonly known as superabsorbent material can be included in absorbent pad 10. In a particular embodiment, absorbent pad 10 can include a mixture of superabsorbent hydrogel-forming particles and wood pulp fluff. Although cellulosic fluff is preferred, one may use synthetic fibers, polymeric fibers, meltblown fibers or a combination of meltblown fibers and natural fibers. Superabsorbent material may be substantially homogeneously mixed with the hydrophilic fibers, or may be otherwise combined into absorbent pad 10.

Absorbent pad 10 may comprise a laminate of fibrous webs and superabsorbent material or other suitable means of maintaining a superabsorbent material in a localized area.

Absorbent pad 10 may have any of a number of shapes. For example, and without limitation, absorbent pad 10 may be rectangular, I-shaped or T-shaped.

The high-absorbency material in absorbent pad 10 can be selected from among natural, synthetic and modified natural polymers and materials. The high absorbency materials can be inorganic materials, such as silica gels, or organic compounds, such as crosslinked polymers. The term crosslinked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

Absorbent pad 10 can include a standard barrier tissue layer 29 covering first surface 12 and a forming tissue layer 31 covering second reference surface 14 of the absorbent pad. Such tissue layers are well known in the art both in terms of materials and functions. The tissue layers generally are permeable to fluids, but retain material of absorbent pad 10 therein. In adult care products, however, a single tissue layer can be wrapped entirely about, and secured to, absorbent pad 10. Other arrangements, containing layers of various materials disposed on surfaces 12, 14, and/or encompassing absorbent pad 10, are contemplated as being within the scope of the invention.

As shown in FIG. 2, inner aperture surface 22 of an aperture 20, comprehends the entirety of the surface of the pad disposed inside opening 33 of the aperture. Thus, inner aperture surface 22 includes the respective bottom 24 as well as sidewalls 25. The density of the absorbent pad proximate inner aperture surface 22 is greater than the overall average density of the absorbent pad. Such higher density thus generally extends along the entire depth of side walls 25 as well as across bottom 24. Such increase in density is generally accompanied by corresponding increased overall structural integrity of absorbent pad 10, whereby structural integrity of absorbent pad 10 is more readily maintained during use of the absorbent pad.

In operation, when an insult of a liquid, such as urine, is poured onto the center of first surface 12 of absorbent pad 10, apertures 20 assist in distributing the urine along the length "L" of the absorbent pad which extends along longitudinal axis 16. First, the free-flowing liquid is received within the void volume inside respective apertures. Second, the denser zones surrounding the apertures, including side walls 25 and bottoms 24, transport the liquid more efficiently than zones of average density. Third, zones of intermediate density between apertures arrayed along length "L," also urge movement of the liquid in a longitudinal direction along length "L" and away from the locus of the insult. Fourth, lower density zones, spaced farther from the denser zones than the zones of intermediate density, absorb the liquid at a higher absorption rate than zones of higher density. Thus the distribution of urine or other exudate in both frontward and rearward longitudinal directions along longitudinal axis 16 is improved by apertures 20 as in FIG. 1.

Absorbent pad 10 of FIG. 1 has an exemplary length of about 21 inches, an exemplary width of about 5.5 inches, and an exemplary thickness "T" of about ¼ inch. This size pad is preferred in adult care products. Other absorbent pads 10, having smaller sizes, are generally preferred for infant care and feminine care products, and are also within the scope of the invention, as are larger size absorbent pads.

In preferred embodiments, the invention contemplates at least 40 of apertures 20 to provide the proper wicking effect without having an adverse consequence on fluid intake. Most embodiments preferably have at least 80 apertures. The large number of apertures provides more locations of increased density located at first surface 12 of absorbent pad 10. The large number of locations improves distribution e.g. wicking of fluid from aperture to aperture. Some embodiments include 120 or more apertures. However, if the number of apertures becomes to large, the corresponding aperture size may be so small that the beneficial effects of the invention are not achieved.

Individual apertures 20 each have a cross-sectional area, across the open cross-sectional area between sidewalls 25 of the respective aperture. Such cross-sectional area is defined transverse to an imaginary axis extending through the absorbent pad 10, e.g. perpendicular to surface 12. The open cross-sectional area typically is from about 0.0025 square inch to about 0.25 square inch. For apertures having a smaller cross-sectional area, the impact on distribution and fluid intake is not significant.

The relationship between the cross-sectional area of apertures 20 and the total surface area of first surface 12 is also an important feature of the invention. The sum of the open cross-sectional areas of apertures 20 should be in a range of from about 5% to about 40% of the total surface area of first surface 12 of absorbent pad 10. For better results, the open cross-sectional area most preferably comprises from about 11% to about 32% of the total surface area of first surface 12.

In FIG. 1, the ratio of the length of individual apertures 20 with respect to length "L" of absorbent pad 10 along longitudinal axis 16 is about 1:20. The invention contemplates the ratio of the length of individual apertures 20 with respect to length "L" being from about 1:10 to about 1:250. The length of a circular aperture 20 can be deduced by utilizing the diameter of the aperture.

While FIG. 2 shows apertures 20 having depths equal to about 90% of thickness "T," depths from about 40% to about 99% of the thickness are permissible with preferred depths being at least 50%, most preferably at least 60%. Further, some apertures 20 can penetrate through bottom 24 of absorbent pad 10 without destroying utility of the pad. Such penetration generally comprises an opening in bottom 24, as at rupture 27, which is smaller, typically substantially smaller, in cross-section than the general open area cross-section defined by the respective aperture 20.

FIG. 1 shows a multiple serpentine pattern for rectangular apertures 20 in first surface 12 of absorbent pad 10. As will be shown by the examples later, the arrangement of apertures 20 with respect to each other has a profound effect on the distribution of fluid in the longitudinal direction of absorbent pad 10. Further, and surprisingly, the arrangement of apertures with respect to each other can actually increase the fluid intake rate of the absorbent pad over a reasonably short test period.

The general nature of apparatus useful for forming apertures 20 in absorbent pads 10, or a continuous absorbent core passing through a nip, is disclosed in U.S. Pat. No. 4,886,632 to Van Iten et al which is hereby incorporated by reference in its entirety. Van Iten et al disclose apparatus for forming apertures of generally uniform open cross-section through the entirety of the thickness of a web. The invention herein utilizes the apparatus of Van Iten et al, with modifications to apparatus and methods of use as discussed hereinafter, to form generally closed-bottom apertures in absorbent pads 10 having much greater thicknesses than the webs of Van Iten et al. U.S. Pat. No. 5,188,625 to Van Iten et al, hereby incorporated by reference in its entirety, discloses using a similar apparatus to form apertures through a liquid-permeable cover layer.

Figure 3:
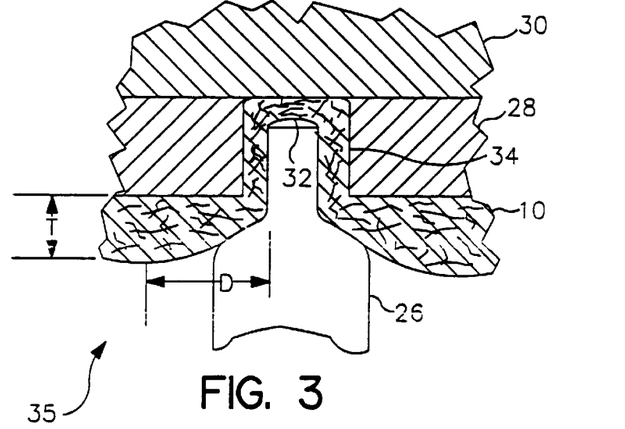
FIG. 3 shows a fragmentary cross-section of apparatus for forming apertures in the absorbent pad according to the invention.

FIG. 3 shows a cross-sectional view of absorbent pad 10 directed through a nip defined by a first member including pin element 26 and a second member including strip 28 and sleeve 30. Pin element 26 has a rounded tip 32, as shown. Rounded tip 32 tends to form a rounded bottom 24 to the aperture so formed, without completely penetrating the thickness "T" of absorbent pad 10. Heating units (not shown) heat respective pin elements 26 and sleeve 30. Strip 28 and sleeve 30 comprise heat conducting material, such as brass, steel or aluminum. Pin elements 26 also comprise heat conducting material, such as brass or steel.

In operation, as absorbent pad 10 moves through the nip, respective heated pin elements 26 of the first member enter heated strip 28, penetrating openings 34. The force of pin elements 26 rotating through the nip pushes respective elements of absorbent pad 10 into openings 34 of strip 28, thus forming apertures 20 in the absorbent pad. The heating of pin elements 26 and strip 28, including outer walls of openings 34, in combination with force exerted at the nip, in absorbent pad 10. softens the fibers while the respective collection of fibers is being acted on by pin element 26. The fibers are thus compressed together while in the heated condition, both at tip 32 and along side walls 34, squeezing the pad between pin element 26 and side walls 25, and between pin element 26 and second surface 14.

While FIGS. 12 and 13 of Van Iten et al '632 show a shoulder on the pin element forming an enlarged area of high density material at the surface of the sheet being processed, this enlarged area can be reduced by tapering the shoulder of the pin element as shown in FIG. 3. The pin element of Van Iten et al breaks the sheet of material being worked. By contrast, in applicants' FIG. 3, the pin element breaks few, if any, fibers, and forces a portion of applicants' thicker absorbent pad 10 into opening 34 where densification is effected.

Preferred temperatures of strip 28 and pin elements 26 are equal to or greater than 300 degrees F. up to about 500 degrees F. The temperature and pressure, in combination, at the nip cause densification of absorbent pad 10 proximate and about apertures 20 so formed by the combination of softening, and simultaneously compressing, the material of the absorbent pad. The heating tends to soften, melt and/or bond fibers of absorbent pad 10 in the compressed dense state shown in FIG. 3. Thus, after the materials of absorbent pad 10 have passed through apparatus 35 of FIG. 3, the combination of compression and heating causes the pad material adjacent apertures 20 to permanently retains its compressed characteristic and corresponding high density, proximate the entirety of aperture surface 22, including side walls and bottoms of the respective apertures. By contrast, the sharp tip of the pin element of Van Iten et al penetrates entirely through the thinner web material, whereby the apertures serve more as conduits for drainage than as reservoirs for containment as in the instant invention.

Pin elements 26 and strip 28 can be cooperatively configured to provide a slotted, but still blind, apertures as shown in FIG. 1. By "blind," we mean that the aperture is open on only one end, for example, the end at surface 12.

Figure 4:
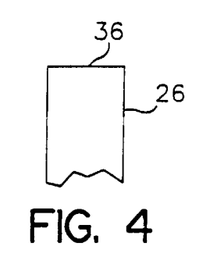
FIG. 4 shows a pictorial view of a first, flat-nosed tip of a pin element for use in the apparatus of FIG. 3.

Other configurations and arrangements of pin elements 26 and cooperating openings 34 are within the scope of the invention. For example, FIG. 4 shows a pin element 26 having a flat end at tip 36. Tip 36 is preferably reasonably chamfered, whereby tip 36 generally creates apertures 20 without complete penetration of absorbent pad 10.

Figure 5:
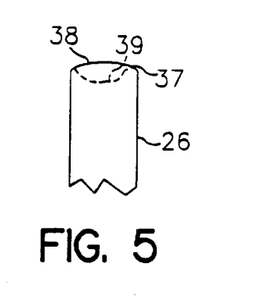
FIG. 5 shows a pictorial view of a second pin element, having an axially inwardly disposed cavity at the tip of the pin element.

FIG. 5 shows a pin element 26 having a recessed end 38 at the tip, including a rim 37, and a cavity 39 extending, from rim 37, axially and transversely inwardly into the end. In usage with apparatus 35 of FIG. 3, the tip having the recessed end forms a pillow of partially densified material in the bottoms of the respective apertures. The density of the pillow so produced is greater than the overall density of absorbent pad 10 and less than the high density pad material at rim 37. Other shapes, such as star shapes, diamond shapes and triangle shapes or other ornamental and/or utilitarian designs can be utilized for pin elements 26.

Pin element diameter, pin element shape, pin element/ strip temperature, pin element pattern, nip gap and nip pressure are among the variables which can be controlled in forming absorbent pad 10. These variables can vary the density and pattern of apertures 20 and thus the overall performance of absorbent pad 10. For example, in some embodiments, pin elements 26 need not be heated.

Referring to FIG. 3, the open aperture/space between the side wall of pin element 26 and side wall 34 of the opening is sized in cooperation with the thickness and strength of the web/pad to be worked, and pin element 26 is configured to be sufficiently blunt that surface-to-surface complete penetration is avoided such that pin element 26 pushes on the pad material at surface 12, pushing the pad material ahead of it, into the opening in strip 28, with corresponding compression and densification of pad material to thereby make a blind, closed-end, aperture in the pad material, with the open end of the aperture opening at surface 12. FIG. 3 illustrates only one such pin element forming only one aperture. Many such pin elements and strip openings can, of course, be used on cooperating registered nip rolls to form such apertured product at production line speeds. Pin element 26 can be pointed, but sufficiently spaced from sleeve 30, to avoid complete penetration of the web/pad being worked.

Figure 6:
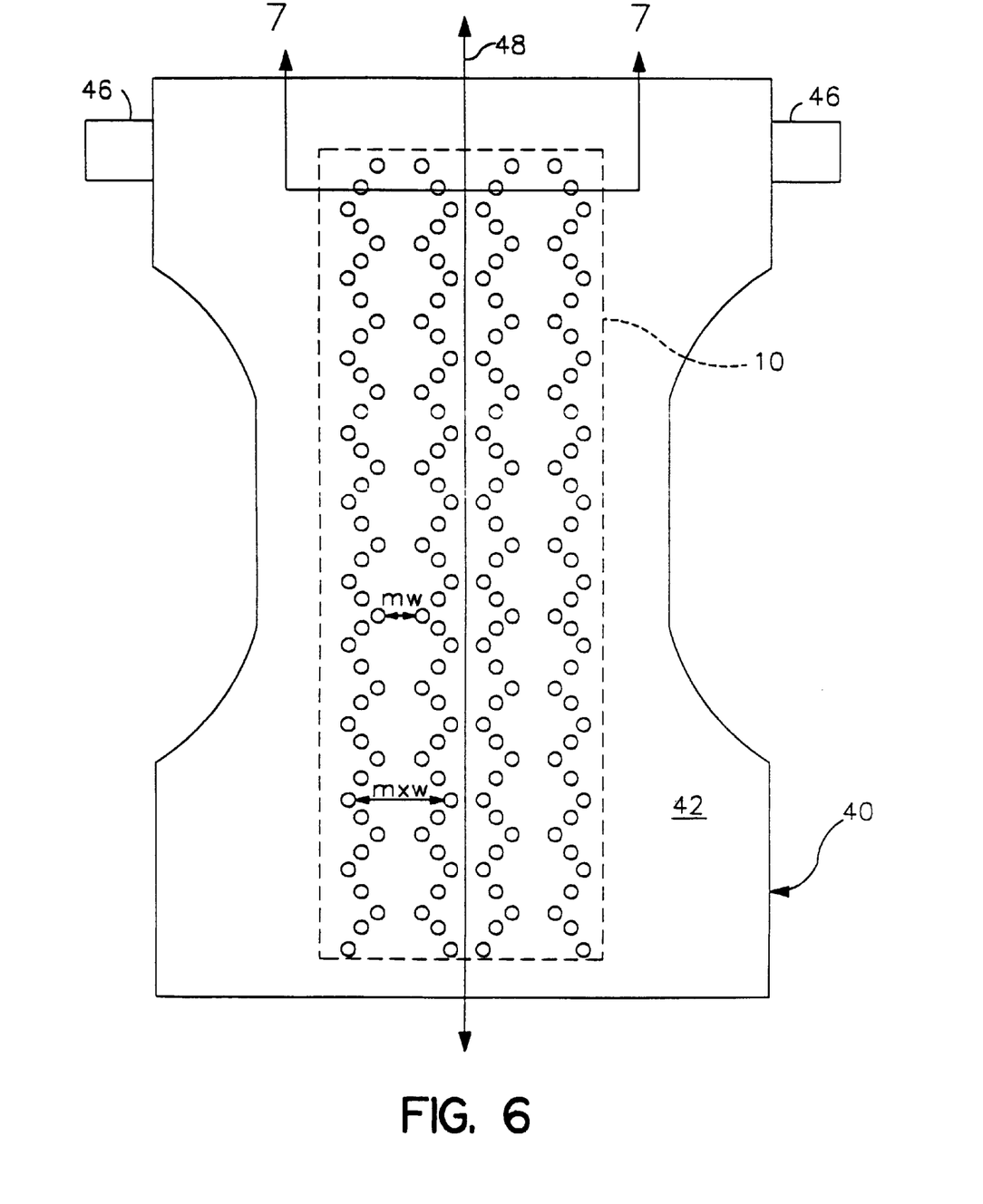
FIG. 6 shows a representative top view of an absorbent article including an absorbent pad of the invention.
Figure 7:
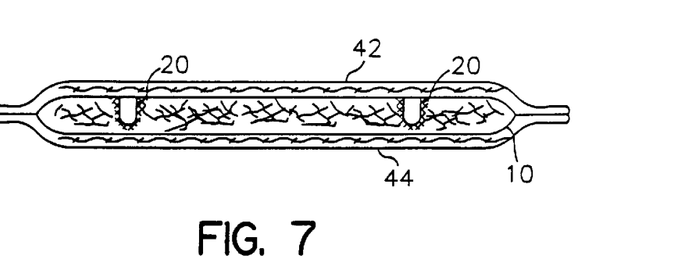
FIG. 7 shows a cross-section of the absorbent article, taken at 7—7 in FIG. 6.

FIGS. 6 and 7 illustrate absorbent pad 10 incorporated into an absorbent article 40. Absorbent article 40 includes absorbent pad 10, bodyside liner 42, outer cover 44, and attachment ears 46. Bodyside liner 42 is generally in surface-to-surface relationship with first surface 12 of absorbent pad 10. Outer cover 44 is generally in surface-to-surface relationship with second surface 14 of absorbent pad 10. The respective elements shown in FIG. 7 can be secured to each other by ultrasonic bonding, adhesives, or other methods well known in the art.

FIG. 6 shows a serpentine pattern of apertures 20 extending along the length of pad 10. Four rows of apertures 20 are shown, each extending along a serpentine path. The pattern of apertures 20 shown in FIG. 6 thus resembles four alternating sine waves. Adjacent paths of apertures 20 alternate between repeating maximum distances "MXW" and repeating minimum distances "MW" between successive apertures in the respective adjacent paths.

Absorbent article 40 in FIG. 6 is applied to the body of a user by securing attachment ears 46 in a rear portion of the absorbent article to a securement surface element (not shown) on outer cover 44 of the front portion. Attachment ears 46 can, for example, comprise the hooks of a hook and loop fastening system. The securement surface element typically comprises a corresponding loop material attached to outer cover 44 in the front portion of absorbent article 40 and adapted to releasably engage with the hook material. Other well known fastening devices can also be used to support absorbent article 40 on the user. For example, a cohesive system, an adhesive fastener system, belts or the like may also be utilized to secure absorbent article 40 to the body of the user.

A suitable bodyside liner 42 may be manufactured from a wide selection of web materials, such as porous foams, reticulated foams, apertured plastic films or natural fibers. For example, bodyside liner 42 may comprise wood or cotton fibers. Other possible materials are synthetic fibers, such as polyester or polypropylene fibers, or a combination of natural and synthetic fibers. Bodyside liner 42 is suitably utilized to help isolate the liquids held in absorbent pad 10 from the skin of a user.

Various woven and nonwoven fabrics may be used for bodyside liner 42. For example, bodyside liner 42 may be composed of a meltblown or spunbonded web of polyolefin fibers. Bodyside liner 42 may also comprise a carded and/or bonded web composed of natural and/or synthetic fibers. Bodyside liner 42 may also be composed of a substantially hydrophobic material wherein the hydrophobic material is treated with a surfactant or otherwise processed to impart a desired level of wettability and hydrophilicity.

In a particular embodiment of the present invention, bodyside liner 42 may comprise a nonwoven, spunbonded, polypropylene fabric composed of about 2.8–3.2 denier fibers formed into a web having a basis weight of about 22 grams per square meter and a density of about 0.06 grams per cubic centimeter. The fabric is then surface treated with about 0.3 weight percent of a surfactant. Bodyside liner 42 may comprise a multiplicity of components or layers which correspond to any of the materials disclosed herein, as well as others known in the art.

Since the web material from which bodyside liner 42 is made has an overall pattern of generally uniform pores, the liner itself is preferably free from larger size apertures or slits formed after the bodyside liner material has been fabricated. Apertures having a diameter of more than about 0.1 inch or slits having a length of more than about 0.25 inch, in the bodyside liner, are not contemplated as being desirable for the disclosed invention. Further, bodyside liner 42 most preferably comprises a web of material, permeable to liquid, and having no apertures or slits of meaningful size or length formed therein.

It is generally preferred that outer cover 44 of absorbent article 40 be formed from a material which is substantially impermeable to liquids. A typical outer cover 44 may be manufactured from a thin plastic film or other flexible liquid-impermeable material. For example, outer cover 44 may be formed from a polyethylene film having a thickness of from about 0.012 millimeters to about 0.051 millimeters. If outer cover 44 should have a more clothlike feeling, it may comprise a polyethylene film laminated to a surface of a nonwoven web, such as a spunbonded web of polyolefin fibers. For example, a polyethylene film having a thickness of about 0.015 millimeters may have thermally or otherwise laminated thereto a spunbond web of polyolefin fibers having a thickness of from 1.5 to 2.5 denier per filament, which nonwoven web has a basis weight of about 24 grams per square meter. Further, outer cover 44 may be formed of a woven or nonwoven fibrous web which has been totally or partially constructed or treated to impart a desired level of liquid impermeability to selected regions that are adjacent or proximate absorbent pad 10. Still further, outer cover 44 may optionally be composed of a micro-porous material which permits vapors to escape from the absorbent pad 10 and through outer cover 44 while preventing liquid exudates from passing through the outer cover 44.

An optional surge layer (not shown) can be located between and in surface-to-surface contact with first surface 12 of absorbent pad 10 and/or bodyside liner 42. The surge layer can comprise materials set forth in U.S. Pat. No. 5,486,166 to C. Ellis and D. Bishop, entitled, "Fibrous Nonwoven Web Surge Layer for Personal Care Absorbent Articles and the Like"; and U.S. Pat. No. 5,490,846 to C. Ellis and R. Everett, entitled, "Improved Surge Management Fibrous Nonwoven Web for Personal Care Absorbent Articles and the Like", the disclosures of which are herein incorporated by reference.

Further, other surge layer materials known in the art can also be utilized.

During construction of absorbent article 40, absorbent pad 10 is positioned between outer cover 44 and bodyside liner 42. Bodyside liner 42 and outer cover 44 are then secured to one another, with absorbent pad 10 therebetween. Optionally, absorbent pad 10 can be secured to outer cover 44 and/or bodyside liner 42. Securement can be effected by adhesives, ultrasonic bonding, stitching or any other well known method of forming an absorbent article. Bodyside liner 42 does not extend substantially into apertures 20 of absorbent pad 10, and specifically does not generally follow side wall 25. Rather, bodyside liner 42 is spaced from bottom 24 and generally from side wall 25.

When absorbent article 40 is mounted on the body of a user, fluid, such as urine, which contacts absorbent pad 10 flows preferentially along the longitudinal direction of the pad and is absorbed into the apertured pad. The serpentine pattern, and relative spacing of apertures 20 from each other, as in FIG. 6, assist in drawing fluid in the longitudinal direction along first surface 12 and from within absorbent pad 10 and apertures 20.

One theory of how absorbent article 40 operates includes a first one of apertures initially receiving liquid. After substantial passage of liquid through bodyside liner 42 and into first aperture 20, the liquid is drawn by capillary effect to a second aperture 20, closely adjacent the first aperture. The apertures of the serpentine pattern are located close enough to one another to generally promote wicking of fluid in the longitudinal direction, by preferentially passing liquid from the one aperture to the second aperture by a capillary effect. Thus, by using capillary effect, as well as other transport properties, fluid can be drawn from the first aperture to the second aperture. The effect can be repeated for other relatively closely spaced apertures along a given (serpentine) path to provide a flow in the longitudinal direction. The pattern of apertures 20 thus provides a path for enhanced wicking and distributing fluid in the longitudinal direction.

As shown in FIG. 6, the apertures in a given serpentine path can be spaced from each other by a distance approximately equal to the diameter of an individual aperture. By so spacing the apertures using e.g. pin elements 26 in forming the apertures, the pad material bridging between such closely adjacent apertures is partially densified/compressed, thus to encourage fluid to flow along the path of apertures in the direction of longitudinal axis 16, along the length of absorbent pad 10, in preference to flow transverse to axis 16.

Another theory regarding the effect of absorbent pad 10 of absorbent article 40 can be expressed as considering density at locations of the absorbent pad. Densified apertures 20 of absorbent pad 10 have a higher density than locations on first surface 12 of the absorbent pad spaced away from the apertures. As described earlier, the density differences are caused by apparatus 35 of FIG. 3 utilizing heated pin elements 26 to form apertures 20.

Further, in theory, first surface areas of absorbent pad 10 up to a first distance "D" from apertures 20 have a higher density than areas of the absorbent pad at locations on the first surface a greater distance than "D" away from the apertures. This is believed to be caused, at least in part, by compression of absorbent pad 10 at first surface 12 caused by physical formation of apertures 20. Thus, besides forming apertures 20 having higher density material, apparatus 35 shown in FIG. 3 draws material of pad 10 toward the several apertures, thereby also increasing the density of absorbent pad 10 at first surface 12 up to distance "D" about each aperture. Therefore, the wicking effect of fluid is increased within the area of absorbent pad 10 which is within the first distance "D" from the respective aperture 20.

In practical terms, the pattern of apertures 20 is preferably arranged such that at least a second aperture 20 is within the first distance "D" from each aperture. Typically second and third apertures are generally arranged at surface 12 on opposing sides of each aperture, thus to define a given one of the serpentine or other paths/lines of apertures, and thus defining a distribution line transporting liquid preferentially longitudinally from the locus of application of the insult. This arrangement increases and promotes wicking of fluid from aperture to aperture. Apertures 20 are generally aligned and spaced in the longitudinal direction to promote distribution of fluid in the longitudinal direction, thereby obtaining use of a greater portion of the first surface 12 of absorbent pad 10 to receive and retain sudden influxes of relatively larger quantities (e.g. body exudate quantities) of fluid.

While the first distance "D" has not been specifically calculated, the invention contemplates that the gradient of the density of material of absorbent pad 10 decreases as the distance increases away from one of apertures 20. Thus the first distance really describes the distance at which the density of absorbent pad 10 at first surface 12 decreases sufficiently to prevent the preferred passage or spreading of fluid to the next one of apertures 20 by capillary effect or the like. The density of material at and adjacent first surface 12 of absorbent pad 10 can continue to decrease as a gradient beyond the first distance from one of apertures 20. The first distance "D" can comprise at least the diameter of an individual one of apertures 20, and may comprise a greater distance. At least one and preferably two apertures 20 aligned in the longitudinal direction are arranged within the first distance of one of the apertures such that fluid is directed from the first one of the apertures along and proximate the first surface of absorbent pad 10 to the other nearby apertures.

While the above theories of operation attempt to explain how improved fluid intake and distribution are obtained, applicants choose to not be bound by any particular theory described above. The test results described below illustrate the surprising advantage gained by the invention.

TEST PROCEDURE

Tests were conducted using a fluid intake flowback evaluation (FIFE) tester (not shown). The FIFE tester has two PLEXIGLASS plates. The top plate of the FIFE tester includes a cylinder having an inner diameter of 2 inches. The top plate has a circular hole formed in the center thereof. The cylinder extends upwardly substantially perpendicular to the surface of the top plate. The cylinder fits within the circular hole and is secured therein by an adhesive. The adhesive permanently secures the cylinder as an integral part of the top plate and prevents liquid from leaking outwardly onto the top surface of the top plate. Pin elements are located near outside corners of the bottom plate. The pin elements align with apertures in the top plate to mount the plates together. A funnel is placed at the top of the cylinder to pour liquid into the test device. The combined mass of the top plate of the FIFE tester including the cylinder, and the funnel is from 900 to 1100 grams.

The test products comprised absorbent pads from DEPEND Extra Absorbency Elastic Leg Undergarments. Absorbent pads 10 had a length of 21 inches, a width of 5.5 inches and a thickness of about 0.25 inch. For purpose of the test, the elastics were removed.

In use, a DEPENDS absorbent article 40, including a bodyside liner 42, an outer cover 44, and absorbent pad, was placed with bodyside liner 42 in surface-to-surface relationship with the top plate of the FIFE tester. Outer cover 44 of absorbent article 40 was in surface-to-surface relationship with the bottom plate of the FIFE tester. Thus absorbent article 40 was located between the top plate and the bottom plate. In use, the bottom plate and top plate of the FIFE tester both define substantially horizontal planes.

Absorbent pad 10 was centered such that the cylinder of the top plate of the FIFE tester was above the center of the absorbent pad and in contact with the bodyside liner. The test began with a first insult of 80 milliliters of saline solution being poured rapidly into the test cylinder via a funnel placed atop the cylinder. Time was recorded from first contact of solution to the absorbent article until complete absorption had occurred (intake time in seconds). Immediately after the liquid was completely absorbed, the length of the pad over which liquid was distributed was measured, thus giving a wicking distance. The liquid was colored to facilitate detection of wicking distance. This measurement was taken from the edges of the colored material on the extreme left point to the extreme right point of the liquid stain along longitudinal axis 48 of absorbent article 40. After a five minute wait, a second 80 milliliter insult was poured into the FIFE cylinder. The time and distance were recorded as for the first insult. A third and final insult of 80 milliliters was applied after another 5 minute delay, and the intake and wicking values were recorded. A final 5 minute delay was added to compare the effects of wicking over time. Only the distance measurement of wicking was taken after the last 5 minute delay.

TEST RESULTS

Figure 8:
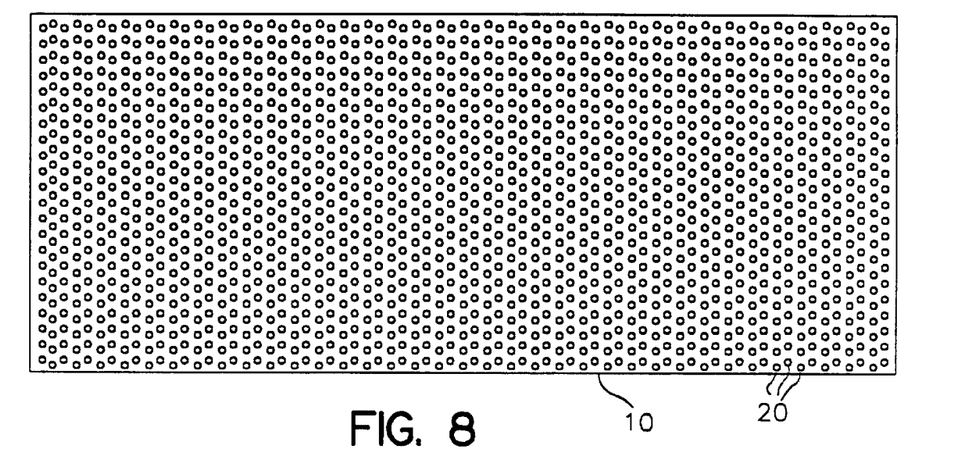
FIG. 8 shows a top view of an absorbent pad that did not function as well as desired.
Figure 9:
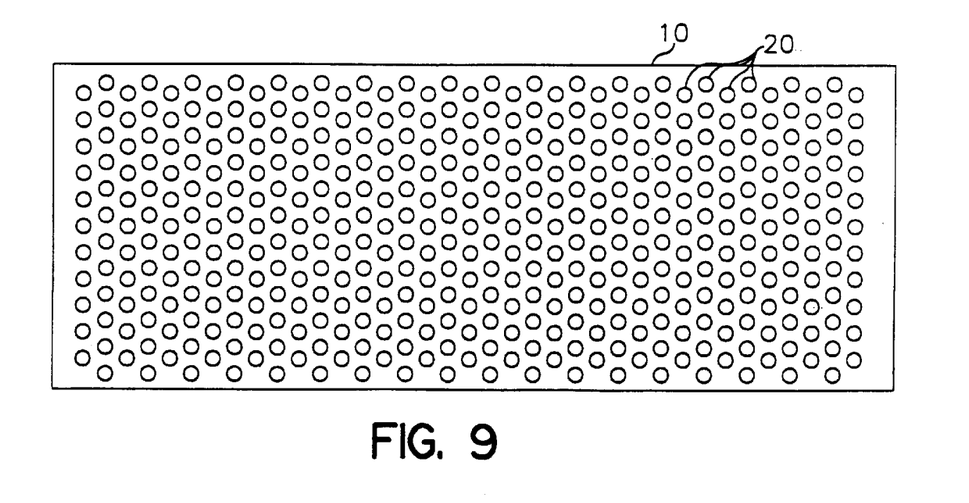
FIG. 9 shows a top view of another absorbent pad of the invention.

FIGS. 8 and 9 show patterns of apertures used to generate test results. FIG. 8 shows a solid pattern (A) of apertures 20 having diameters of 0.109 inch. FIG. 9 shows a solid pattern (B) of apertures 20 having diameters of 0.25 inch. FIG. 6 shows an absorbent article 40 including absorbent pad 10 having a serpentine pattern (C) of apertures 20 which gained the best overall test results. An absorbent pad was tested having no apertures to use as a control for the other experiments. Results are listed as follows. The wicking distance measured is inches in the longitudinal direction between the leading edges of the colored material on opposing sides of the colored material resulting from the insult, measured along the longitudinal axis 48 of the absorbent article. The wicking distance is measured at the time the cylinder of fluid has been completely absorbed by the absorbent pad. The last measurement is taken 5 minutes after the third insult of fluid has been absorbed by the absorbent pad.

TABLE 1

WICKING DISTANCE SUMMARY

| PATTERN | FIRST INSULT | SECOND INSULT | THIRD INSULT | AFTER 5 MINUTES |
|---|---|---|---|---|
| Control | 6.0 in. | 7.7 in. | 9.9 in. | 12.4 in. |
| Pattern A | 7.3 in. | 10.2 in. | 13.4 in. | 16.1 in. |
| Pattern B | 6.2 in. | 9.0 in. | 12.7 in. | 15.9 in. |
| Pattern C | 6.2 in. | 9.8 in. | 13.3 in. | 16.8 in. |

As shown by the above data, all of the patterns of higher density apertures 20 have increased wicking in the longitudinal direction over that of the Control, which had no apertures. The intake time for each insult equals the time required for the entire quantity of fluid in the test cylinder to be absorbed by the absorbent pad. The intake time differed greatly for the tested patterns as follows.

TABLE 2

INTAKE TIME SUMMARY

| PATTERN | FIRST INSULT | SECOND INSULT | THIRD INSULT |
|---|---|---|---|
| Control | 27.8 sec. | 57.5 sec. | 57.3 sec. |
| Pattern A | 40.1 sec. | 61.1 sec. | 80.1 sec. |
| Pattern B | 14.2 sec. | 32.2 sec. | 33.4 sec. |
| Pattern C | 11.0 sec. | 31.0 sec. | 31.4 sec |

Pattern A comprised a full apertured pattern as shown in FIG. 8. About 1600 apertures, each having a diameter of about 0.109 inch, are present in Pattern (A). As shown in Table 2 above, the intake time for the absorbent pad having pattern (A) of apertures 20 exceeded the intake time of the Control absorbent pad. Thus, the embodiment of Pattern (A) is not suitable for use in an absorbent pad 10 where intake time is an important consideration.

Pattern (B) is another fully apertured pattern as shown in FIG. 9. About 660 apertures having a diameter of about 0.25 inch make up Pattern (B) of FIG. 9. Surprisingly, Pattern (B) had improved intake time compared to both the Control absorbent pad and the Pattern (A) pad. It is interesting to note that the improvement of Pattern (B) over Control, from the second insult to the third insult, remained at about 25 seconds. This observation supports the theory that the open space cross-section of the large apertures of Pattern (B) had an influence on the intake time. Initially, the 14 seconds intake time improvement over the Control absorbent pad could be attributed to the fluid filling voids created by the apertures faster than absorption could occur. The 25 second improvement seen in the second insult resulted because the control remained saturated while the open volume in the apertures of pattern (B) was again open to retain fluid and because of improved wicking of fluid. Thus the same improvement for the third insult was likewise achieved.

Pattern (C) taken from absorbent article 40 of FIG. 6 provided the best overall results. The four serpentine patterns of Pattern (C) comprise about 160 apertures, each having a diameter of about 0.25 inch. The performance of Pattern (C) was very good as the test results indicate. The intake time of Pattern (C) was better than the intake time for Pattern (B). The longitudinal wicking distance for Pattern (C) was also better than the wicking distance for Pattern (B) or any other tested pattern having an improved intake time. Thus Pattern (C) shown in FIG. 6 provided highly desirable results for use in an absorbent article.

Figure 10:
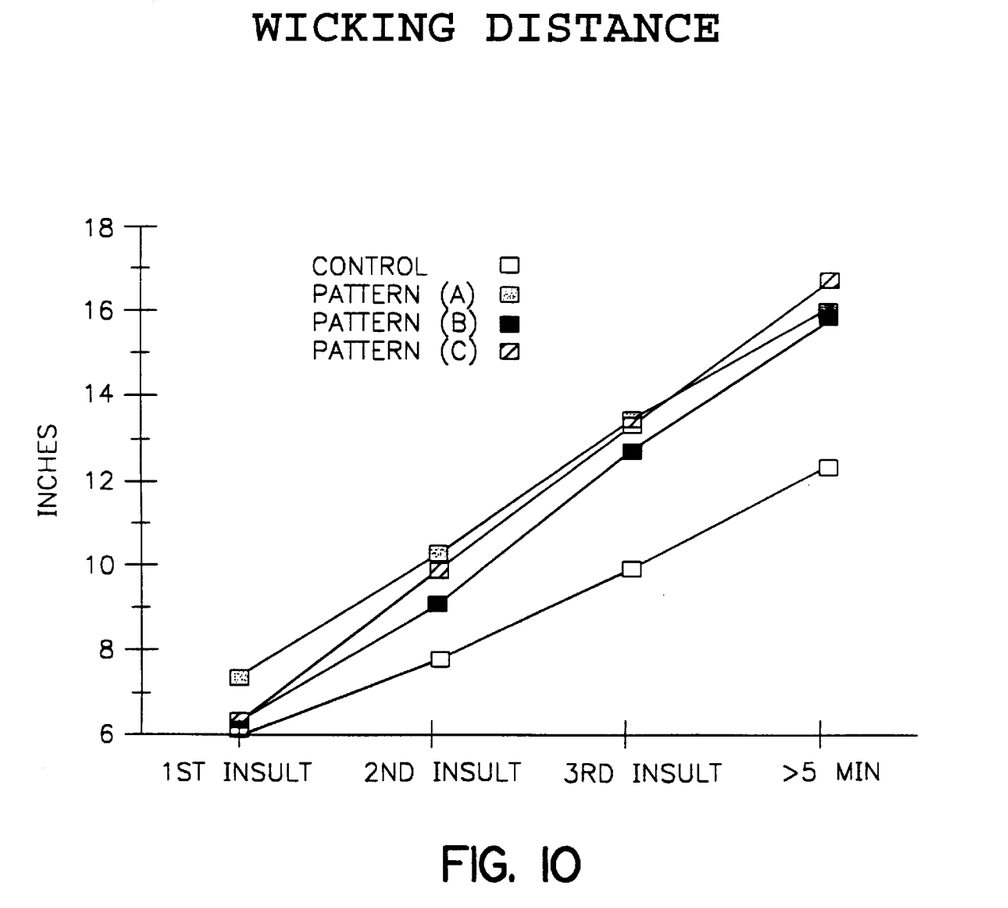
FIG. 10 is a graph showing comparative wicking distance as a function of aperture size and arrangement.
Figure 11:
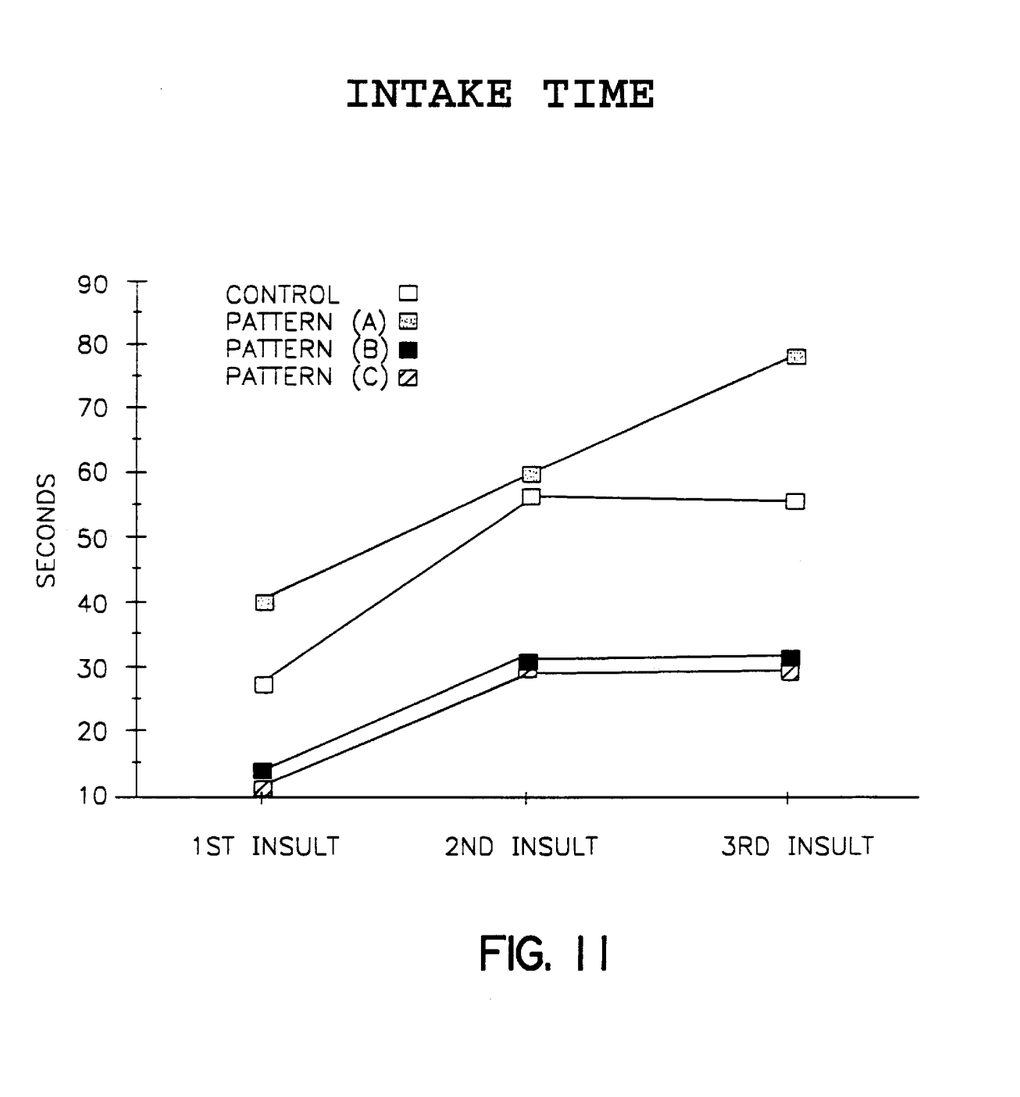
FIG. 11 is a graph showing comparative intake time as a function of aperture size and arrangement.

The Graphs of FIGS. 10 and 11 better show the relationship between intake time and wicking distance for the Control pattern and Patterns (A)–(C). In conclusion, the surface area of apertures, the number of apertures, the depth of apertures, the density of pad material adjacent the apertures, and especially the distance between apertures all are important factors in designing an improved absorbent pad for use in absorbent articles.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

Having thus described the invention, what is claimed is:

1. An absorbent pad for use in an absorbent article, said absorbent pad having a length and a width, opposing first and second surfaces, a thickness between the first and second surfaces, and an outer layer of said absorbent pad at the first surface, said outer layer being permeable to fluid, the first surface of said absorbent pad having apertures therein, said apertures forming a longitudinal pattern on the first surface and extending from the first surface inwardly of said absorbent pad, substantially all of said apertures terminating in bottoms of the respective said apertures, said apertures forming said longitudinal pattern being spaced sufficiently close to each other that an aqueous liquid is transferred from aperture to aperture by capillary effect to increase the distribution of fluid along the length of said absorbent pad relative to distribution of fluid transverse to the length of said absorbent pad.

2. An absorbent pad as in claim 1, the first surface of said absorbent pad having at least 80 of said apertures therein.

3. An absorbent pad as in claim 1, said apertures having depths of at least about 40% of the thickness of said absorbent pad.

4. An absorbent pad as in claim 1, said apertures having depths of from about 40% to about 99% of the thickness of said absorbent pad.

5. An absorbent pad as in claim 1, said apertures each having an open cross-sectional area thereacross, of from about 0.0025 square inch to about 0.25 square inch.

6. An absorbent pad as in claim 1, the first surface defining a total surface area on a first side of said absorbent pad, the open cross-sectional area of said apertures comprising from about 5% to about 40% of the total surface area of the first surface of said absorbent pad.

7. An absorbent pad as in claim 1, the first surface defining a total surface area on a first side of said absorbent pad, the open cross-sectional area of said apertures comprising from about 11% to about 32% of the total surface area of the first surface of said absorbent pad.

8. An absorbent pad as in claim 1, each said aperture having an aperture surface extending inwardly into said absorbent pad, including along side walls and said bottom of the respective aperture, the density of said absorbent pad proximate the aperture surface being greater than the overall average density of said absorbent pad about substantially the entirety of the aperture surface.

9. An absorbent pad as in claim 1, the pattern of said apertures comprising a serpentine pattern, extending along the length of said absorbent pad.

10. An absorbent pad as in claim 1, the pattern of said apertures comprising four serpentine elements extending along the length of said absorbent pad, the respective serpentine elements being spaced from each other across the width of said absorbent pad.

11. An absorbent pad as in claim 1, the pattern of said apertures contributing to increasing the fluid intake rate of said absorbent pad.

12. An absorbent pad as in claim 1, said apertures contributing to improved integrity of said absorbent pad.

13. An absorbent pad as in claim 1, each said bottom comprising an inner bottom surface thereof facing generally toward the first surface, and an outer bottom surface thereof facing away from the first surface, said outer bottom surface extending outwardly, in said absorbent pad, from the second surface at respective said apertures.

14. An absorbent article including an absorbent pad of claim 1, said absorbent pad being located between a bodyside liner and an outer cover.

15. An absorbent pad for use in an absorbent article, said absorbent pad having a length and a width, opposing first and second surfaces, a thickness between the first and second surfaces, and an outer layer of said absorbent pad at the first surface, said outer layer being permeable to fluid, the first surface of said absorbent pad having apertures extending from the first surface inwardly of said absorbent pad, substantially all of said apertures terminating in bottoms of the respective said apertures, said apertures having lengths and widths, defining corresponding elongate shapes, the orientations of the lengths of said elongate apertures corresponding to the length of said absorbent pad, said apertures forming a longitudinal pattern spaced sufficiently close to each other that an aqueous liquid is transferred from aperture to aperture by capillary effect to increase longitudinal fluid distribution, relative to distribution of fluid transverse to the length of said absorbent pad.

16. An absorbent pad as in claim 15, said absorbent pad having a longitudinal axis, the ratio of the average length of said elongate apertures to the length of said absorbent pad along the longitudinal axis being from about 1:10 to about 1:250.

17. An absorbent pad as in claim 15, said absorbent pad comprising at least 80 said apertures.

18. An absorbent pad as in claim 15, said absorbent pad comprising at least 40 said apertures.

19. An absorbent pad as in claim 15, said apertures having depths of from about 40% to about 99% of the thickness of said absorbent pad.

20. An absorbent pad as in claim 15, said apertures each having an open cross-sectional area thereacross, of from about 0.0025 square inch to about 0.25 square inch.

21. An absorbent pad as in claim 15, the first surface defining total surface area on a first side of said absorbent pad, the open cross-sectional area of said apertures comprising from about 5% to about 40% of the total surface area of the first surface of said absorbent pad.

22. An absorbent pad as in claim 15, the first surface defining a total surface area on a first side of said absorbent pad, the open cross-sectional area of said apertures comprising from about 11% to about 32% of the total surface area of the first surface of said absorbent pad.

23. An absorbent pad as in claim 15, said apertures forming a pattern on the first surface of said absorbent pad, said pattern increasing the fluid intake rate of said absorbent pad.

24. An absorbent pad as in claim 23, the pattern of said apertures contributing to increasing the distribution of fluid along the length of said absorbent pad relative to distribution of fluid transverse to the length of said absorbent pad.

25. An absorbent pad as in claim 15, each said bottom comprising an inner bottom surface thereof facing generally toward the first surface, and an outer bottom surface thereof facing away from the first surface, said outer bottom surface extending outwardly, in said absorbent pad, from the second surface at respective said apertures.

26. An absorbent article including an absorbent pad of claim 15, said absorbent pad being located between a bodyside liner and an outer cover.

27. An absorbent article having a front portion, a rear portion, a crotch portion connecting said front and rear portions, and a longitudinal axis extending through said front, rear and crotch portions, said absorbent article comprising:
 (a) an absorbent pad having opposing first and second surfaces and a thickness between the first and second surfaces, said absorbent pad having a multiplicity of apertures therein, said multiplicity of apertures forming a longitudinal pattern, said longitudinal pattern of said apertures spaced sufficiently close to each other that an aqueous liquid is transferred from aperture to aperture by capillary effect to increase the distribution of fluid along the length of said absorbent pad relative to distribution of fluid transverse to the length of said absorbent pad; and
 (b) a bodyside liner mounted in surface-to-surface relationship to the first surface of said absorbent pad, said bodyside liner being spaced from absorbent material located inwardly in said absorbent pad from the first surface.

28. An absorbent article as in claim 27, said multiplicity of apertures comprising at least 80 said apertures.

29. An absorbent article as in claim 27, said multiplicity of apertures comprising at least 40 said apertures.

30. An absorbent article as in claim 27, said apertures having depths of from about 40% to about 99% of the thickness of said absorbent pad.

31. An absorbent article as in claim 27, said apertures each having an open cross-sectional area thereacross, of from about 0.0025 square inch to about 0.25 square inch.

32. An absorbent article as in claim 27, the first surface defining a total surface area on a first side of said absorbent pad, the open cross-sectional area of said apertures comprising from about 11% to about 32% of the total surface area of the first surface of said absorbent pad.

33. An absorbent article as in claim 27, said apertures having lengths and widths, defining corresponding elongate shapes, the lengths of said elongate apertures corresponding to the length of said absorbent pad.

34. An absorbent article as in claim 33, said absorbent article having a longitudinal axis, the ratio of the average length of said elongate apertures to the length of said absorbent pad along the longitudinal axis being from about 1:10 to about 1:250.

35. An absorbent article as in claim 27, said apertures forming said pattern contributing to increasing the fluid intake rate of said absorbent pad.

36. An absorbent article as in claim 35, said pattern of said apertures comprising a serpentine pattern, said serpentine pattern having a pattern length, extending along the length of said absorbent pad.

37. An absorbent article as in claim 35, said pattern of said apertures comprising four serpentine elements extending along the length of said absorbent pad, the respective serpentine elements being spaced from each other across the width of said absorbent pad.

38. An absorbent article as in claim 27, each said aperture having an aperture surface extending inwardly into said absorbent pad, including along side walls and a bottom of the respective aperture, the density of said absorbent pad proximate the aperture surface being greater than the overall average density of said absorbent pad about substantially the entirety of the aperture surface.

39. An absorbent article as in claim 27, said bodyside liner comprising a water permeable material.

40. An absorbent pad for use in an absorbent article, said absorbent pad having a length and a width, having opposing first and second surfaces, a thickness between the first and second surfaces, and apertures extending from the first surface inwardly into said absorbent pad, said apertures forming a longitudinal aperture pattern promoting wicking of fluid along the length of said absorbent pad relative to wicking of fluid transverse to the length of said absorbent pad, a first said aperture being longitudinally spaced close enough to a second said aperture to preferentially pass liquid from said first aperture, along the length of said absorbent pad, to said second aperture by a capillary effect, thus preferentially drawing liquid along the length of said absorbent pad.

41. An absorbent pad as in claim 40, the first surface of said absorbent pad having at least 80 apertures therein.

42. An absorbent pad as in claim 40, said apertures having depths of at lease about 40% of the thickness of said absorbent pad.

43. An absorbent pad as in claim 40; said apertures each having an open cross-sectional area thereacross, of from about 0.0025 square inch to about 0.25 square inch.

44. An absorbent pad as in claim 40, the first surface defining a total surface area on a first side of said absorbent pad, the open cross-sectional area of said apertures comprising from about 11% to about 32% of the total surface area of the first surface of said absorbent pad.

45. An absorbent pad as in claim 40, each said aperture having an aperture surface extending inwardly into said absorbent pad, including along side walls and a bottom of the respective aperture, the density of said absorbent pad proximate the aperture surface being greater than the overall average density of said absorbent pad about substantially the entirety of the aperture surface.

46. An absorbent pad as in claim 40, said pattern of said apertures comprising a serpentine pattern, said serpentine pattern having a pattern length, extending along the length of said absorbent pad.

47. An absorbent pad as in claim 40, said pattern comprising four serpentine elements extending along the length of said absorbent pad, the respective serpentine elements being spaced from each other across the width of said absorbent pad.

48. An absorbent pad as in claim 40, said pattern of said apertures contributing to increasing the fluid intake rate of said absorbent pad.

49. An absorbent pad as in claim 40, said apertures contributing to improved integrity of said absorbent pad.

50. An absorbent pad for use in an absorbent article, said absorbent pad having a length and a width, a first surface, an opposing second reference surface, and a thickness between the first surface and the second reference surface, the first surface of said absorbent pad having an array of apertures therein, said apertures extending from the first surface inwardly of said absorbent pad, said apertures terminating in bottoms of the respective said apertures, each said bottom comprising an inner bottom surface thereof facing generally toward the first surface, an outer bottom surface thereof facing away from the first surface, said outer bottom surfaces extending outwardly in said absorbent pad from the second reference surface, said array of apertures forming a longitudinal pattern spaced sufficiently close to each other that an aqueous liquid is transferred from aperture to aperture by capillary effect to increase longitudinal fluid distribution, relative to distribution of fluid transverse to the length of said absorbent pad.

51. An absorbent pad as in claim 50, said apertures having depths of from about 40% to about 99% of the thickness of said absorbent pad.

52. An absorbent pad as in claim 50, the first surface defining a total surface area on a first side of said absorbent pad, the open cross-sectional area of said apertures comprising from about 11% to about 32% of the total surface area of the first surface of said absorbent pad.

53. An absorbent pad as in claim 50, each said aperture having an aperture surface extending inwardly into said absorbent pad, including along side walls and a bottom of the respective aperture, the density of said absorbent pad proximate the aperture surface being greater than the overall average density of said absorbent pad about substantially the entirety of the aperture surface.

54. An absorbent pad as in claim 50, said apertures forming a pattern on the first surface of said absorbent pad, said pattern contributing to increasing the distribution of fluid along the length of said absorbent pad relative to distribution of fluid transverse to the length of said absorbent pad.

55. An absorbent pad as in claim 54, said pattern of said apertures comprising a serpentine pattern, said serpentine pattern having a pattern length, extending along the length of said absorbent pad.

56. An absorbent pad as in claim 54, said pattern of said apertures contributing to increasing the fluid intake rate of said absorbent pad.

57. An absorbent pad as in claim 50, said apertures contributing to improved integrity of said absorbent pad.

\* \* \* \* \*

UNITED STATES PATENT AND TRADEMARK OFFICE
CERTIFICATE OF CORRECTION

PATENT NO. : 5,925,026
DATED      : July 20, 1999
INVENTOR(S) : David Jerome Arteman et al.

It is certified that error appears in the above-identified patent and that said Letters Patent is hereby corrected as shown below:

Column 3, line 24, change "10" to --12--; line 40, after "Thus" insert --,--.
Column 5, line 50, before "surface" insert --first--.
Column 6, line 57, after "10" delete ".".
Column 10, line 27, after "pad" insert --10--; line 29, after "pad" insert --10--; line 30, after "apertures" insert --20--.

In the Claims:
Claim 42, line 2, change "lease" to --least--.

Signed and Sealed this

Twenty-seventh Day of February, 2001

Attest:

NICHOLAS P. GODICI

Attesting Officer          Acting Director of the United States Patent and Trademark Office